(12) United States Patent
Keränen et al.

(10) Patent No.: US 11,730,599 B2
(45) Date of Patent: Aug. 22, 2023

(54) MEDICAL SYSTEM FOR ANNULOPLASTY

(71) Applicant: Medtentia International Ltd Oy, Espoo (FI)

(72) Inventors: Olli Keränen, Bjärred (SE); Hans-Reinhard Zerkowski, Kreuzlingen (CH); Jouko Vallikari, Espoo (FI)

(73) Assignee: HVR Cardio Oy, Espoo (FI)

( * ) Notice: Subject to any disclaimer, the term of this patent is extended or adjusted under 35 U.S.C. 154(b) by 0 days.

(21) Appl. No.: 16/648,866

(22) PCT Filed: Sep. 21, 2018

(86) PCT No.: PCT/EP2018/075713
§ 371 (c)(1),
(2) Date: Mar. 19, 2020

(87) PCT Pub. No.: WO2019/057947
PCT Pub. Date: Mar. 28, 2019

(65) Prior Publication Data
US 2020/0281722 A1    Sep. 10, 2020

Related U.S. Application Data

(60) Provisional application No. 62/561,838, filed on Sep. 22, 2017.

(51) Int. Cl.
*A61F 2/24* (2006.01)
(52) U.S. Cl.
CPC .......... *A61F 2/2466* (2013.01); *A61F 2/2445* (2013.01); *A61F 2/2451* (2013.01);
(Continued)
(58) Field of Classification Search
CPC .... A61F 2/2451; A61F 2/2442; A61F 2/2445; A61F 2/2466; A61F 2230/0091;
(Continued)

(56) References Cited

U.S. PATENT DOCUMENTS

2003/0083538 A1* 5/2003 Adams .................. A61F 2/2451
600/16
2003/0130730 A1* 7/2003 Cohn .................. A61B 17/3478
623/2.36
(Continued)

FOREIGN PATENT DOCUMENTS

EP    2620125 A1    7/2013

OTHER PUBLICATIONS

Ozcan Cetin, et al Coronary Sinus Diameter to Inferior Vena Cava Diameter Ratio in the Diagnosis of Cardiac Tamponade: A Novel Approach, Journal of Computer Assisted Tomography: Jul. 8, 2020—vol. 44—Issue 4—p. 599-604 (Year: 2020).*
(Continued)

*Primary Examiner* — Keri J Nelson
*Assistant Examiner* — Rebecca Lynee Zimmerman
(74) *Attorney, Agent, or Firm* — Patent Grove AB; Tomas Friend

(57) ABSTRACT

An annuloplasty device is disclosed for treating a defective mitral valve having an annulus, comprising a removable and flexible elongate displacement unit for temporary insertion into a coronary sinus (CS) adjacent the valve, wherein the displacement unit has a delivery state for delivery into the CS, and an activated state to which the displacement unit is temporarily and reversibly transferable from said delivery state, the displacement unit comprises a proximal reversibly expandable portion, a distal anchoring portion being movable in relation to the proximal expandable portion in a longitudinal direction of the displacement unit to said activated state in which the shape of the annulus is modified to a modified shape, wherein the proximal expandable portion is reversibly foldable to an expanded state for positioning against a tissue wall at the entrance of the CS, and wherein the distal anchoring portion comprises an inflatable unit.

11 Claims, 7 Drawing Sheets

(52) U.S. Cl.
CPC . *A61F 2230/0091* (2013.01); *A61F 2250/001* (2013.01); *A61F 2250/0003* (2013.01); *A61F 2250/0098* (2013.01)

(58) Field of Classification Search
CPC ........ A61F 2250/0003; A61F 2250/001; A61F 2250/0098; A61F 2/2448
See application file for complete search history.

(56) References Cited

U.S. PATENT DOCUMENTS

| | | | |
|---|---|---|---|
| 2004/0133220 A1* | 7/2004 | Lashinski | A61F 2/2466 606/151 |
| 2005/0267574 A1 | 12/2005 | Cohn et al. | |
| 2006/0129051 A1* | 6/2006 | Rowe | A61B 1/00082 600/508 |
| 2008/0065205 A1* | 3/2008 | Nguyen | A61F 2/2466 623/2.36 |
| 2016/0095705 A1* | 4/2016 | Keranen | A61F 2/2445 623/2.36 |

OTHER PUBLICATIONS

International Search Report for International Application No. PCT/EP2018/075713, dated Jan. 7, 2019 (3 pages).

* cited by examiner

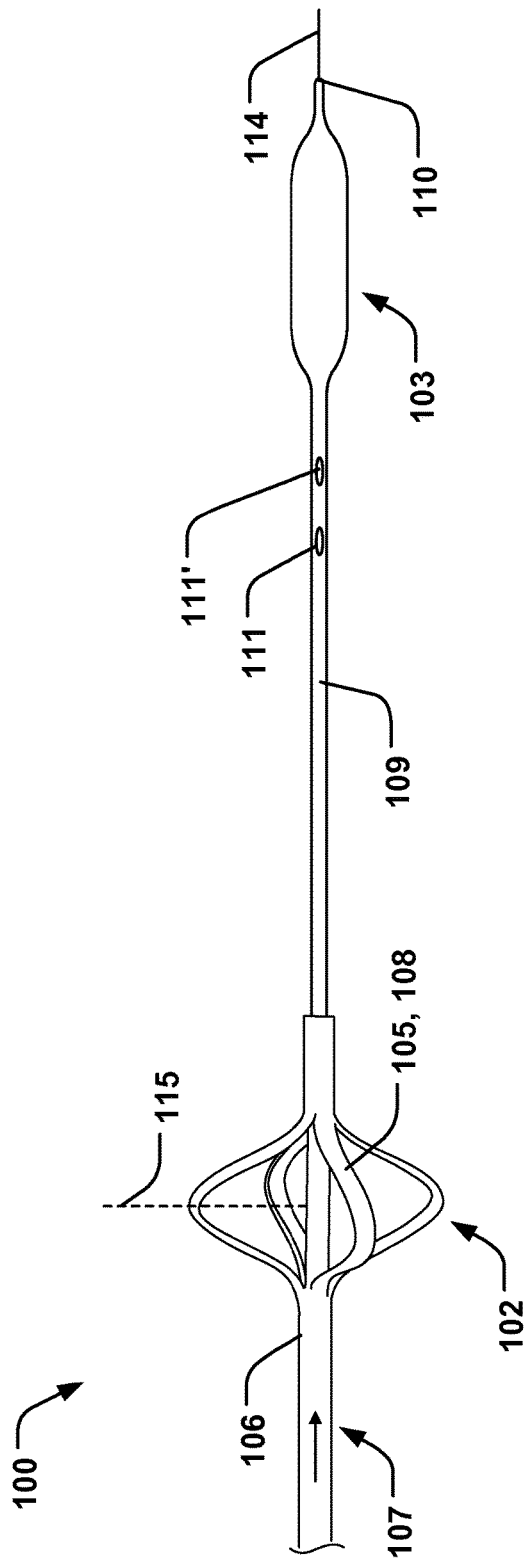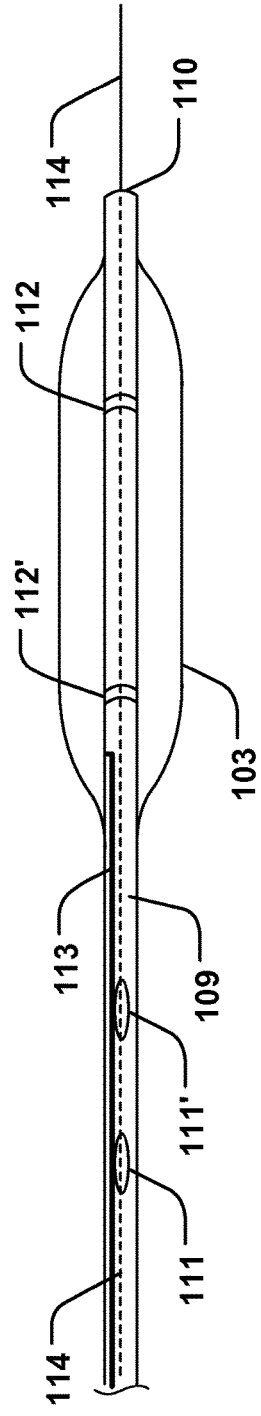
Fig. 2a
Fig. 2b

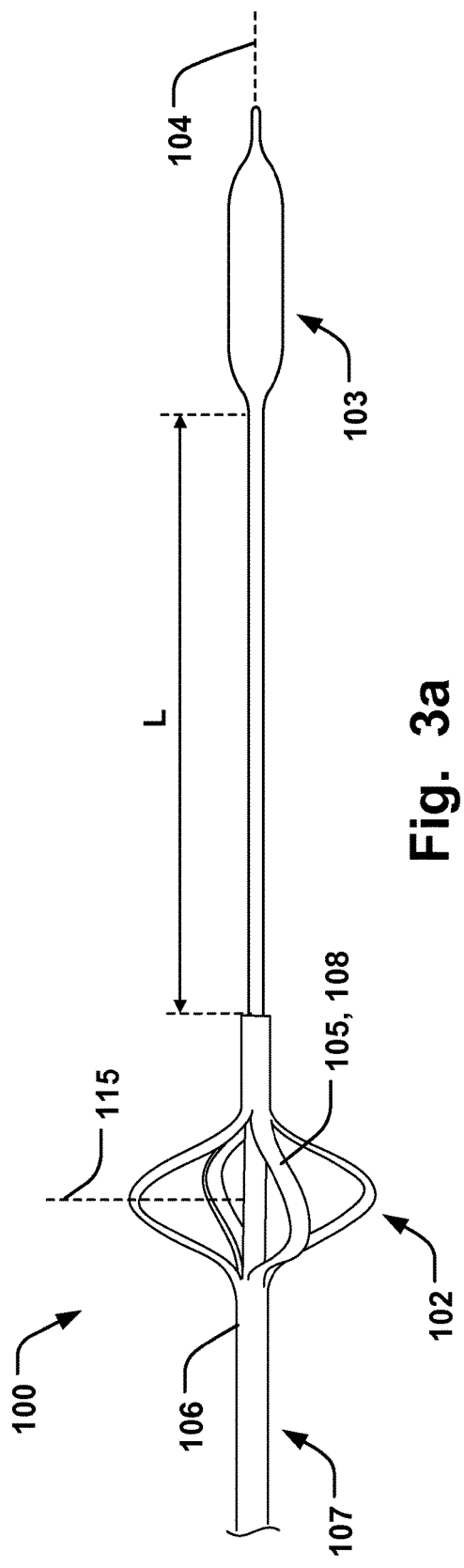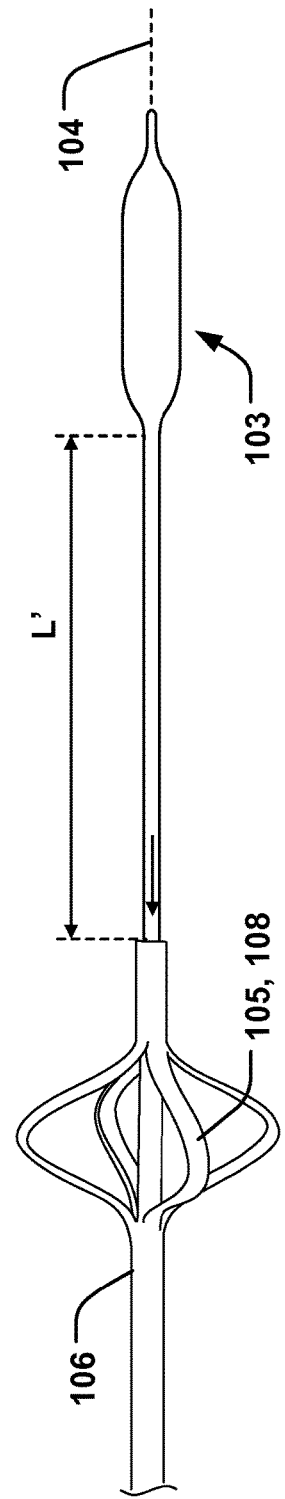
Fig. 3a
Fig. 3b

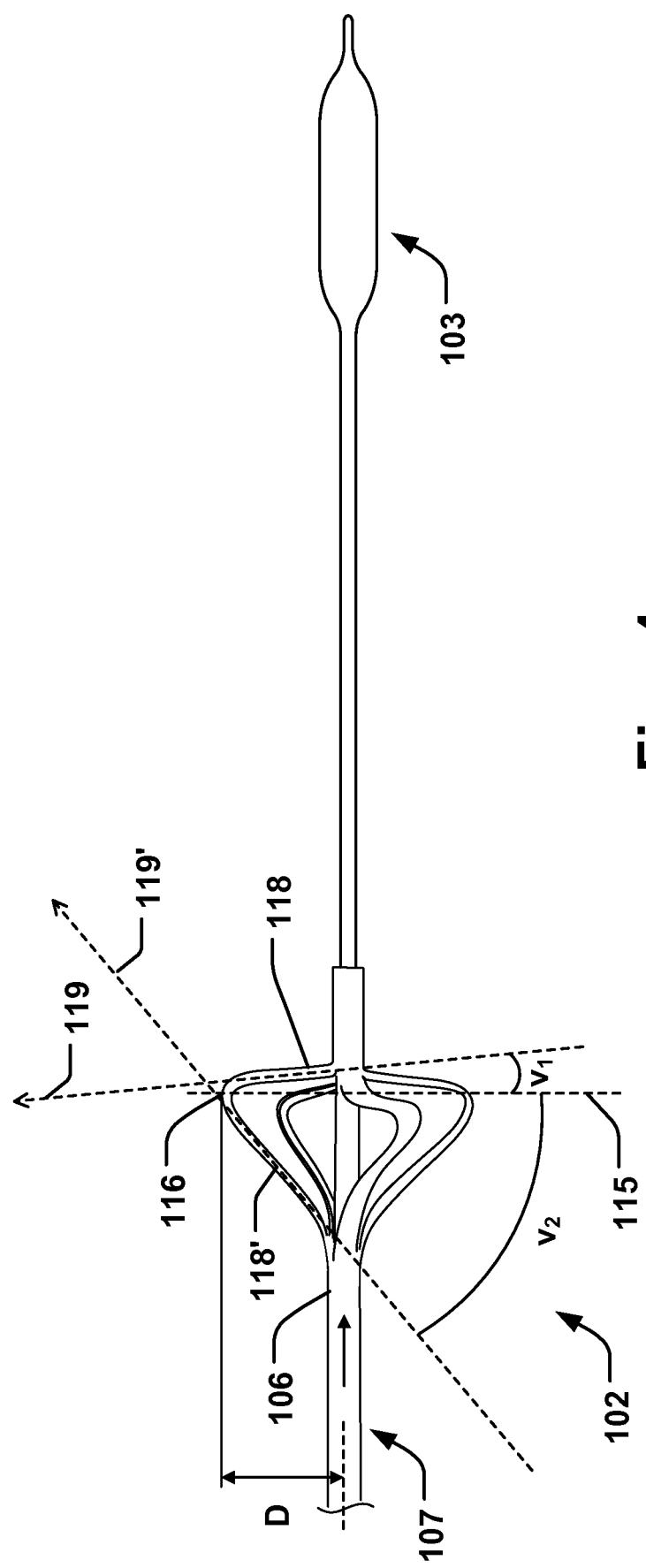

MEDICAL SYSTEM FOR ANNULOPLASTY

CROSS-REFERENCE TO RELATED APPLICATIONS

This application claims priority to International Application No. PCT/EP2018/075713, filed Sep. 21, 2018 and titled "MEDICAL SYSTEM FOR ANNULOPLASTY," which in turn claims priority from a Provisional Application having application No. 62/561,838, filed Sep. 22, 2017, titled "MEDICAL SYSTEM FOR ANNULOPLASTY," both of which are incorporated herein by reference in their entireties.

FIELD OF THE INVENTION

This invention pertains in general to the field of annuloplasty devices for treating a defective mitral valve. More particularly the invention relates to a medical system of devices for treating a defective mitral valve via coronary sinus and an annuloplasty implant for fixation of the annulus, and a method therefore.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure.

Implants have previously been introduced into the coronary sinus (CS) in order to affect the shape of the valve annulus and thereby the valve function. U.S. Pat. No. 6,210,432 and WO02/062270 discloses such implant that is aimed to replace annuloplasty rings. Permanent implants have several disadvantageous effects, for example since they are implanted into the CS which is a source for later complications. Thus, a problem with the prior art implants in the CS is that such implants may be less effective in retaining the desired geometry of the annulus. It may be necessary for the implants to be positioned in the CS for a lengthy time in order to sustain the correct function of the valve. This pose significant requirements on the long-term function of the implant, that may not be as effective as annuloplasty rings to start with. A further problem with prior art is thus that complex and difficult-to-operate devices must be deployed in the CS, that may require frequent adjustment and repositioning to ensure the correct function over time. Another problem with prior art devices is the traumatic effects on the CS itself, due to fixation structures that must ensure the correct position of the device in the CS over time. Another problem is to ensure that a significant part of the annulus is reshaped while providing for atraumatic engagement with the anatomy.

The above problems may have dire consequences for the patient and the health care system. Patient risk is increased.

Hence, an improved annuloplasty device for performing downsizing and reshaping of the valve annulus would be advantageous and in particular allowing for ensuring long-term functioning, less complex procedure, and less traumatic effects on the anatomy and increased patient safety. Also, a method of downsizing and reshaping the mitral valve annulus with such medical annuloplasty device would be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect an annuloplasty device is provided for treating a defective mitral valve having an annulus, comprising a removable and flexible elongate displacement unit for temporary insertion into a coronary sinus (CS) adjacent the valve, wherein the displacement unit has a delivery state for delivery into the CS, and an activated state to which the displacement unit is temporarily and reversibly transferable from said delivery state, the displacement unit comprises a proximal reversibly expandable portion, a distal anchoring portion being movable in relation to the proximal expandable portion in a longitudinal direction of the displacement unit to said activated state in which the shape of the annulus is modified to a modified shape, wherein the proximal expandable portion is reversibly foldable to an expanded state for positioning against a tissue wall at the entrance of the CS, and wherein the distal anchoring portion comprises an inflatable unit.

According to a second aspect medical system for treating a defective mitral valve having an annulus is provided. The system comprises in combination; an annuloplasty device for treating a defective mitral valve having an annulus, comprising a removable and flexible elongate displacement unit for temporary insertion into a coronary sinus (CS) adjacent the valve, wherein the displacement unit has a delivery state for delivery into the CS, and an activated state to which the displacement unit is temporarily and reversibly transferable from said delivery state, the displacement unit comprises a proximal reversibly expandable portion, a distal anchoring portion being movable in relation to the proximal expandable portion in a longitudinal direction of the displacement unit to said activated state in which the shape of the annulus is modified to a modified shape, wherein the proximal expandable portion is reversibly foldable to an expanded state for positioning against a tissue wall at the entrance of the CS, and wherein the distal anchoring portion comprises an inflatable unit. The system comprises an annuloplasty device for permanent fixation at the mitral valve annulus by annuloplasty of the valve when said modified shape is obtained, wherein said annuloplasty device comprises a loop structure, such as a helix-shaped loop structure, configured to be positioned on either side of said valve to retain said modified shape of the annulus, wherein at least a portion of the loop structure conforms to a curvature of said annulus.

According to a third aspect a method is provided for treating a defective mitral valve having an annulus, the method comprises inserting a flexible and removable elongate displacement unit in a delivery state into a coronary sinus (CS) adjacent said valve, positioning a proximal expandable portion against a tissue wall at the entrance of said CS, anchoring a distal anchoring portion comprising an inflatable unit inside the CS by expanding of the inflatable unit, activating the displacement unit in an activated state whereby the distal anchoring portion is moved in a longitudinal direction of the displacement unit to reduce a distance (L) between the distal anchoring portion and the proximal expandable portion such that the shape of the annulus is modified to a modified shape, fixating an annuloplasty device at the mitral valve annulus when said modified shape is obtained, whereby said annuloplasty device comprises a loop structure, such as a helix-shaped loop structure, positioned on either side of the valve to retain the modified shape of the annulus, wherein at least a portion of the loop structure is conformed to a curvature of said annulus, removing the elongate displacement unit after temporary activation in the activated state.

Further examples of the invention are defined in the dependent claims, wherein features for the second and subsequent aspects are as for the first aspect mutatis mutandis.

Some examples of the disclosure provide for long-term functioning of the mitral valve.

Some examples of the disclosure provide for less complex downsizing procedures of the mitral valve.

Some examples of the disclosure provide for a reduced risk of damaging the anatomy such as the CS.

Some examples of the disclosure provide for a secure downsizing while at the same time reducing the risk of damaging the anatomy such as the CS.

Some examples of the disclosure provide for improved downsizing of the mitral valve annulus while ensuring an atraumatic procedure.

Some examples of the disclosure provide for reduced risk of long-term negative effects of CS implants.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 2a is a schematic illustration of an annuloplasty device, with an expanded proximal portion, according to one example;

FIG. 2b is a detailed view of the distal portion of the annuloplasty device in FIG. 2a, according to one example;

FIGS. 3a-b are schematic illustrations of an annuloplasty device, with different lengths between proximal and distal portions, according to one example;

FIG. 4 is a schematic illustration of an annuloplasty device according to one example;

DESCRIPTION OF EMBODIMENTS

Figure 1A:
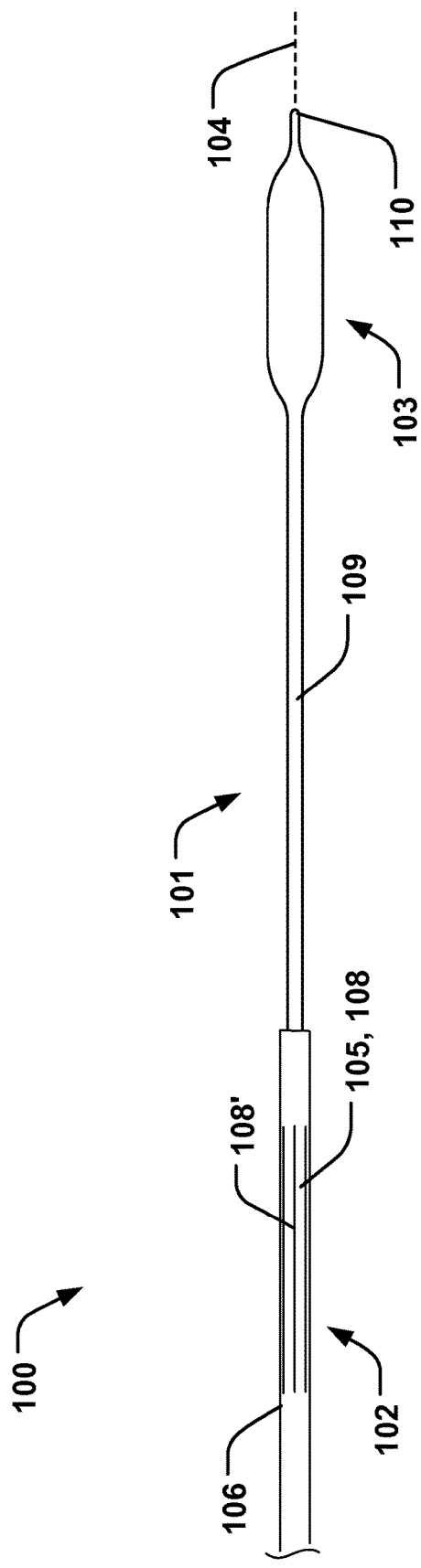
FIG. 1a is a schematic illustration of an annuloplasty device according to one example.

Specific embodiments of the invention will now be described with reference to the accompanying drawings.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 5:
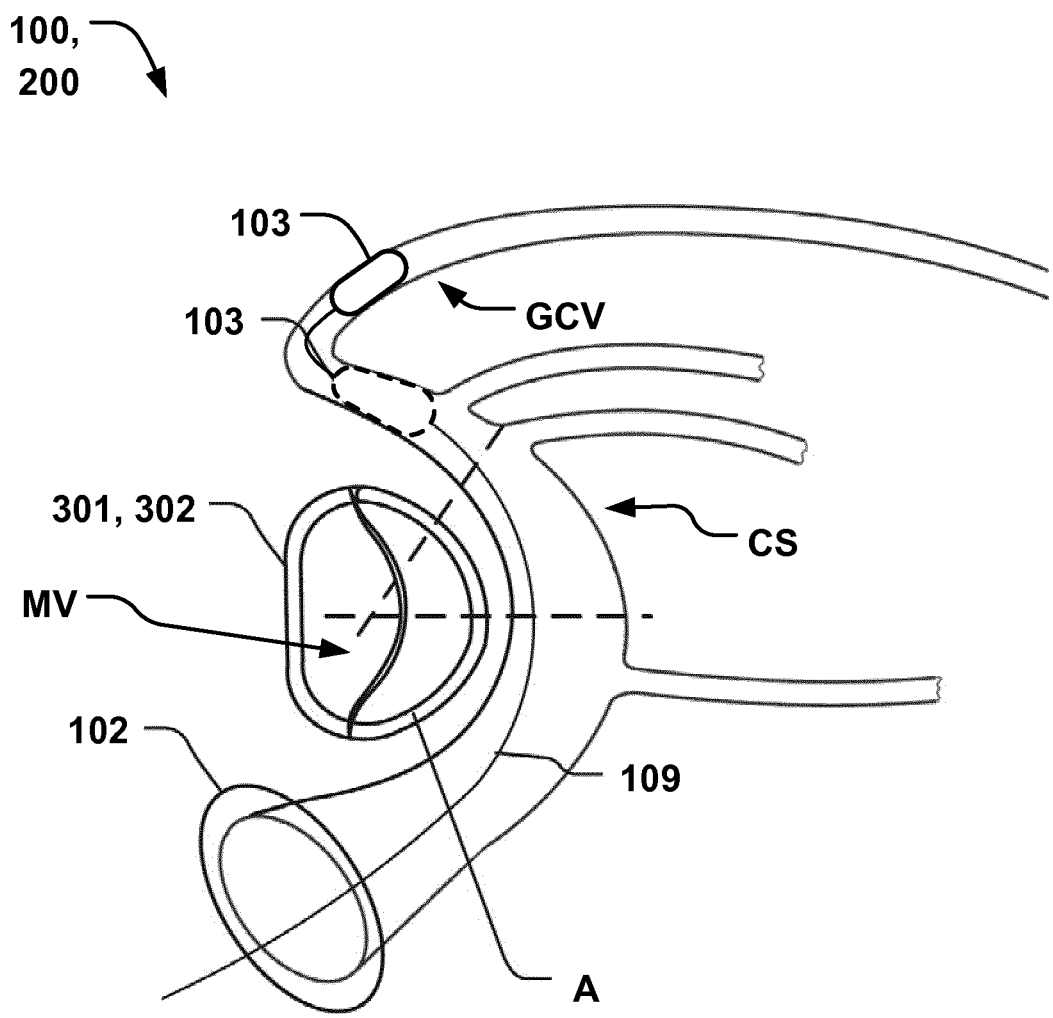
FIG. 5 is a schematic illustration of a medical system for treating a defective mitral valve when placed in the heart, according to one example.

FIG. 1 schematically illustrates an annuloplasty device 100 for treating a defective mitral valve having an annulus. The annuloplasty device 100 comprises a removable and flexible elongate displacement unit 101 for temporary insertion into a coronary sinus (CS) adjacent the mitral valve. FIG. 5 is an illustration of the heart showing the CS in relation to the mitral valve (MV) in a top-down view. The CS lies adjacent the MV and follows a curvature around the annulus (A) of the MV. The displacement unit 101 has a delivery state for delivery into the CS, and an activated state to which the displacement unit 101 is temporarily and reversibly transferable from said delivery state. The displacement unit 101 comprises a proximal reversibly expandable portion 102, and a distal anchoring portion 103 being movable in relation to the proximal expandable portion in a longitudinal direction 104 of the displacement unit 101 to said activated state, so that a distance (L) between the proximal portion 102 and the distal anchoring portion 103 can be varied as seen in FIGS. 3a-b. In the activated state, the annuloplasty device 100, when placed in the CS, modifies the annulus to a modified shape where the annulus is downsized and the leaflets may co-apt. The proximal expandable portion 102 is reversibly foldable to an expanded state for positioning against a tissue wall at the entrance of the CS. FIG. 5 illustrates schematically how the proximal expandable portion 102 is positioned outside the CS, for pushing against the wall at the entrance of the CS. The distal anchoring portion 103 comprises an inflatable unit, such as a balloon. This provides for efficient and non-traumatic fixation of the distal end of the displacement unit 101, which in combination with the efficient anchoring against the wall of the CS by the proximal portion 102, allows for an efficient transfer of a contracting force of the proximal and distal portions 102, 103, towards each other. This allows for an effective modification of the radius of curvature of the CS to facilitate modifying the shape of the valve annulus. The modified shape of the annulus may then be fixed by attachment of an annuloplasty device 301 to the valve, as described further below, before removing the displacement unit 101. The proximal expandable portion 102 and the distal anchoring portion 103 may be connected to different sheaths or wires, that may be independently movable in the longitudinal direction 104 to provide for varying the distance (L) as illustrated in FIGS. 3a-b.

Figure 1B:
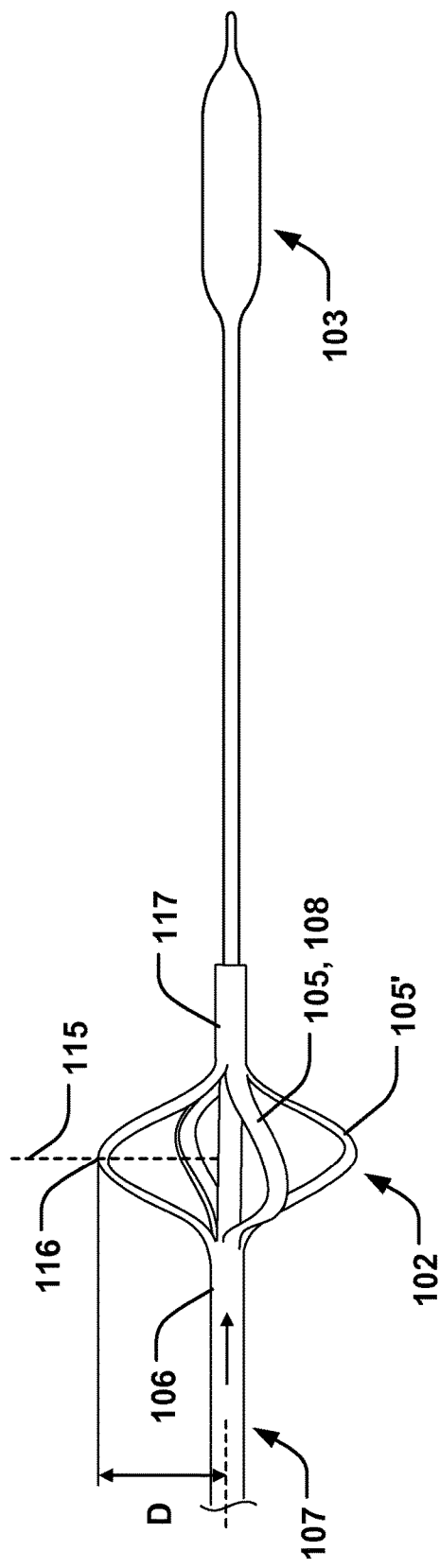
FIG. 1b is a schematic illustration of an annuloplasty device, with an expanded proximal portion, according to one example.

The proximal expandable portion 102 may comprise expandable bows 105 extending in the longitudinal direction 104, as schematically illustrated in e.g. FIGS. 1a-b. Having such expandable bows 105 provides for to further lessen the risk of damaging the tissue at the entrance of the CS, since a soft apposition against the tissue may be provided, in absence of sharp edges or kinks. Having the bows 105 extending in the longitudinal direction 104 also facilitates a symmetric engagement against the tissue wall, with an even transfer of force around the entrance to the CS, hence allowing for a robust anchoring. The longitudinal extension of the bows 105 also provides for facilitated expansion of the bows 105 by applying a force to the bows 105 in the longitudinal direction 104. The bows 105 may extend with a curvature forming an apex 116 at the middle portion of the bow 105, where the apex 116 is positioned at the maximum expanded diameter of the proximal expandable portion 102. Both portions of the bow 105 extending from the apex 116 may extend in the longitudinal direction 104. A plurality of bows 105, 105', may be arranged circumferentially so that a force may be applied symmetrically and evenly around the tissue wall.

The expandable bows 105 may be connected to a sheath 106 and may be configured to be expanded in a radial direction 115, perpendicular to the longitudinal direction 104, by pushing a proximal portion 107 of the sheath 106 towards the distal anchoring portion 103, as indicated in FIG. 1b (see arrow adjacent sheath 106). This provides for a facilitated deployment of the bows 105 to the expanded configuration. The sheath 116 may be pushed in relation to a distal portion 117 attached distally to the bows 105. The compressive force between the distal portion 117 and the proximal portion 107 may thus push the bows 105 radially outwards. It is conceivable however that the bows 105 may comprise a shape-memory material having a tendency to assume the expanded configuration in its relaxed state, and that the bows may be confined in an outer sheath (not shown) being pulled back so that the bows 105 spring into the expanded configuration.

The bows 105 may comprise elongated ribs 108 formed in the sheath 106 by elongated cuts 108' in the sheath 106, extending in the longitudinal direction 104, as schematically illustrated in FIG. 1a. This provides for a simple and robust construction from which the expandable bows 105 provided. The bows 105 may thus be formed from the same material as the sheath 106. The mentioned material may be a soft flexible material which is non-traumatic to tissue. In the collapsed configuration seen in FIG. 1a, the ribs 108, i.e. the soon to be expanded bows 105, extend in the longitudinal direction 104, and provides for a compact radial profile.

The bows 105 may be placed equidistantly around a circumference of the sheath 106. As elucidated above, this may provide for an even distribution of the anchoring force.

When the proximal expandable portion 102 is folded to the expanded state, the expandable bows 105 may extend with a curvature forming an apex 116 positioned at a maximum expanded diameter (D) of the proximal expandable portion 102. Each of the bows 105 may extend with two expanded sections 118, 118', towards the apex 116, as illustrated in FIG. 4. The two expanded sections 118, 118', may comprise a proximal expanded section 118' and a distal expanded section 118. The distal expanded section 118 is configured to be arranged against the tissue wall at the entrance of the CS. At least a portion of the distal expanded section 118 may extend in a first direction 119 forming a first angle ($v_1$) with the radial direction 115, and at least a portion of the proximal expanded section 118' may extend in a second direction 119' forming a second angle ($v_2$) with the radial direction 115. The first angle ($v_1$) may be less than the second angle ($v_2$), as further shown in the example of FIG. 4. This provides for improving the support of the proximal expandable portion 102 against the tissue wall at the entrance of the CS. I.e. since the angle ($v_1$) of the distal expanded section 118 is reduced compared to the second angle ($v_2$) the distal expanded section 118 will be more parallel to the radial direction 115 than the proximal expanded section 118'. Since the tissue wall is typically also substantially parallel to the radial direction 115, the surface area of the distal expanded section 118 in contact with the tissue wall will increase. This provides for a more stable and robust anchoring point with less risk of movement of the in the proximal expandable portion 102 relative the tissue wall in the longitudinal direction 104. In some examples, the first direction 119 may be substantially parallel with the radial direction 115, which provides for a stable positioning of the proximal expandable portion 102 relative the tissue wall at the entrance of the CS.

The maximum expanded diameter (D) of the proximal expandable portion 102 may be at least three times the diameter of the CS. In some examples the ratio of the maximum expanded diameter (D) of the proximal expandable portion 102 to the diameter of the CS is in the range 3-5. In some examples the aforementioned ratio may be in the range 3.5-4.5, which provides for a particular advantageous anchoring of the proximal expandable portion 102, while maintaining a compact and easy to use device 100.

The elongate displacement unit 101 may comprise a lumen 109 extending in the longitudinal direction 104. The lumen may have a distal opening 110 arranged distally of the inflatable unit 103, and at least one proximal opening 111, 111', arranged between the inflatable unit 103 and the proximal expandable portion 102, as schematically illustrated in FIGS. 2a-b. This provides for minimizing the risk of occlusion in the CS, since blood may flow between the distal opening 110 and the at least one proximal opening 111, 111'. The number of openings 111, 111', may be varied to optimize the flow and minimize the risk of occlusion.

The annuloplasty device 100 may comprise a guide wire 114 arranged to extend inside the lumen 109 and to exit the lumen 109 at the distal opening 110. This provides for facilitated positioning of the elongate displacement unit 101. The lumen 109 may thus allow for both guiding of the guide wire 114 and for transport of blood between proximal openings 111, 111', and the distal opening 110, which provides for a robust and compact annuloplasty device 100.

The elongate displacement unit 101 may comprise at least one radiopaque marker 112, 112', arranged inside the inflatable unit 103, as schematically illustrated in FIG. 2b. The radiopaque marker 112, 112', is visible in medical imaging methods. The radiopaque marker 112, 112', may be arranged in the elongate displacement unit 101 and at a portion thereof extending through the inflatable unit 103. This provides for determining the position of the inflatable unit 103 while maintaining a robust and low-profile annuloplasty device 100.

The annuloplasty device 100 may comprise an inflation lumen 113 connected to inflatable unit 103 and configured to deliver an inflation medium to the inflatable unit 103, as schematically illustrated in FIG. 2b.

As mentioned, the distance (L) between the proximal expandable portion 102 and the distal anchoring portion 103 in the longitudinal direction 104 may be decreased to a reduced distance (L') when the displacement unit 101 is transferred from the delivery state to the activated state, as schematically illustrated in FIGS. 3a-b.

A medical system 200 is provided for treating a defective mitral valve having an annulus, as schematically illustrated in FIG. 5. The system 200 comprises in combination an annuloplasty device 100 as described above in relation to FIGS. 1-4, and an annuloplasty implant 301. As described, the annuloplasty device 100 comprises a removable and flexible elongate displacement unit 101 for temporary insertion into a coronary sinus (CS) adjacent the valve, wherein the displacement unit 101 has a delivery state for delivery into the CS, and an activated state to which the displacement unit 101 is temporarily and reversibly transferable from said delivery state. The displacement unit 101 comprises a proximal reversibly expandable portion 102, a distal anchoring portion 103 being movable in relation to the proximal expandable portion 102 in a longitudinal direction 104 of the displacement unit 101 to said activated state in which the shape of the annulus is modified to a modified shape. The proximal expandable portion 102 is reversibly foldable to an expanded state for positioning against a tissue wall at the entrance of the CS, and the distal anchoring portion 103 comprises an inflatable unit. The annuloplasty implant 301 is configured for permanent fixation at the mitral valve annulus by annuloplasty of the valve when said modified shape is obtained. The annuloplasty device 301 comprises a loop structure 302, such as a helix-shaped loop structure, configured to be positioned on either side of said valve to retain said modified shape of the annulus, wherein at least a portion of the loop structure conforms to a curvature of said annulus. The system 200 thus provides for the advantageous benefits as described in relation to the annuloplasty device 100 above, e.g. providing for efficient downsizing of the valve annulus and for subsequent fixation of the modified shape by the annuloplasty implant 301 as schematically illustrated in FIG. 5.

The annuloplasty implant 301 may comprise a first support ring and a second support ring, being arranged in a coiled configuration around an axial direction. The first and second support rings may be adapted to be arranged on opposite sides of native heart valve leaflets to pinch said leaflets. The annuloplasty implant 301 may have shape-memory properties, such that the first and second supports may assume an elongated configuration when delivered in a catheter, whereupon the first and second supports may assume the coiled configuration when ejected from the delivery catheter. The annuloplasty implant 301 may also comprise closed single-loop rings, such as D-shaped rings, or open single-loop rings, such as C-shaped annuloplasty rings.

Figure 6A:
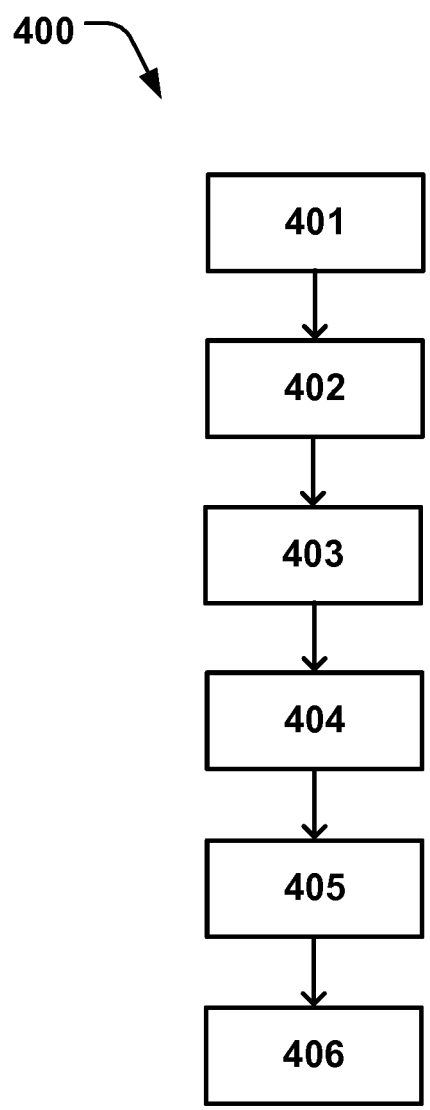
FIG. 6a is a flow chart of a method for treating a defective mitral valve according to one example.

FIG. 6a illustrates a method 400 for treating a defective mitral valve. The order in which the steps of the method 400 are illustrated should not be construed as limiting and it is conceivable that the order in which the steps of the method 400 is carried out may be varied. The method 400 comprises; inserting 401 a flexible and removable elongate displacement unit 101 in a delivery state into a coronary sinus CS adjacent said valve; positioning 402 a proximal expandable portion 102 against a tissue wall at the entrance of said CS; anchoring 403 a distal anchoring portion 103 comprising an inflatable unit inside the CS by expanding of the inflatable unit; activating 404 the displacement unit 101 in an activated state whereby the distal anchoring portion 103 is moved in a longitudinal direction 104 of the displacement unit 101 to reduce a distance (L) between the distal anchoring portion 103 and the proximal expandable portion 102 such that the shape of the annulus is modified to a modified shape. The method 400 comprises fixating 405 an annuloplasty implant 301 at the mitral valve annulus when said modified shape is obtained, whereby the annuloplasty implant 301 comprises a loop structure 302, such as a helix-shaped loop structure, positioned on either side of the valve to retain the modified shape of the annulus. At least a portion of the loop structure is conformed to a curvature of the annulus. The method comprises removing 406 the elongate displacement unit 101 after temporary activation in the activated state. The method 400 thus provides for the advantageous benefits as described above in relation to the device 100 and system 200 and FIGS. 1-5.

Figure 6B:
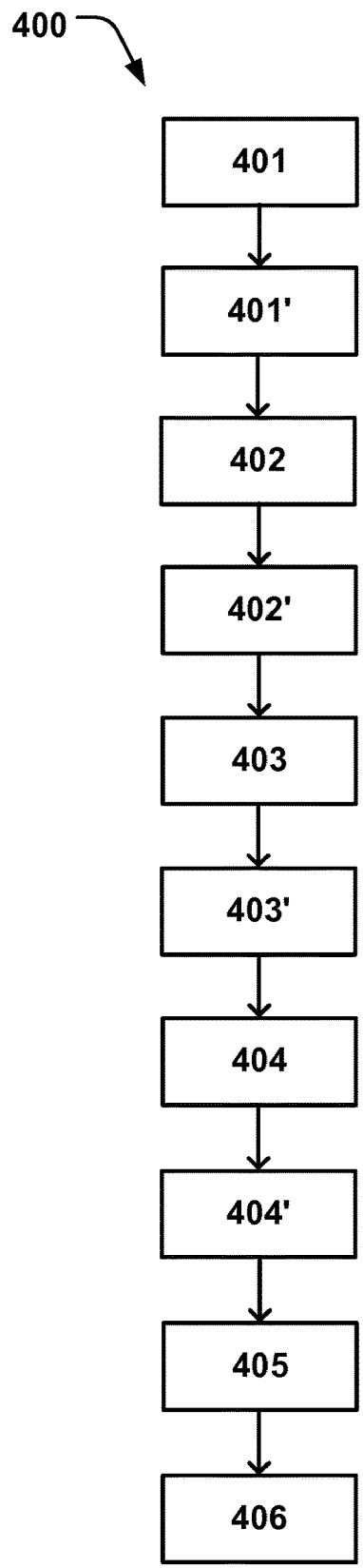
FIG. 6b is a flow chart of a method for treating a defective mitral valve according to one example.

FIG. 6b illustrates another flow chart of a method 400 for treating a defective mitral valve. The order in which the steps of the method 400 are illustrated should not be construed as limiting and it is conceivable that the order in which the steps of the method 400 is carried out may be varied.

Positioning of the proximal expandable portion 102 may comprise expanding 402' bows 105 extending in the longitudinal direction 104 for apposition against the tissue wall. The method 400 may further comprise exerting 404' of a force against the tissue wall in the longitudinal direction 104 towards the distal anchoring portion 103.

Anchoring the distal anchoring portion 103 may comprise inflating 403' the inflatable unit 103 in the great cardiac vein and/or, in the anterior interventricular branch or vein, and/or in the posterior vein and/or in the posterior ventricular vein of the heart. This provides for improving the anchoring force of the distal anchoring portion 103.

The method 400 may comprise guiding 401' the elongate displacement unit 101 along a guide wire 114 arranged to extend inside a lumen 109 of the elongate displacement unit 101. The guide wire 114 may be arranged to exit the lumen at an opening 110 distally of the inflatable unit 103. The lumen 109 may have a proximal opening 111 arranged between the inflatable unit 103 and the proximal expandable portion 102.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:
1. An annuloplasty device for treating a defective mitral valve having an annulus, said annuloplasty device comprising a removable and flexible elongate displacement unit for temporary insertion into a coronary sinus adjacent the mitral valve, the displacement unit comprising:
  a proximal, reversibly expandable portion comprising a soft, flexible first sheath;
  a distal anchoring portion comprising an inflatable unit attached to a second sheath that is movable in relation to the proximal expandable portion in a longitudinal direction of the displacement unit and configured for anchoring the distal anchoring portion to the inside of the coronary sinus when the inflatable unit is inflated; and
  an inflation lumen inside the second sheath configured to deliver an inflation medium to the inflatable unit;
  wherein said first sheath comprises cuts extending in said longitudinal direction that form reversibly expandable soft, flexible bows configured to expand in a radial direction, perpendicular to said longitudinal direction, by pushing a proximal portion of said first sheath toward the distal anchoring portion when said distal anchoring portion is anchored in the coronary sinus; and wherein the proximal anchoring portion, when expanded, is configured to be arranged against a tissue wall outside the entrance to the coronary sinus.

2. Annuloplasty The annuloplasty device according to claim 1, wherein the proximal expandable portion is configured such that, when expanded, the bows extend with a curvature forming an apex positioned at a maximum expanded diameter (D) of the proximal expandable portion, whereby each of the bows extend with a proximal expanded section and a distal expanded section with the distal expanded section configured to be arranged against said tissue wall and wherein at least a portion of the distal expanded section extends in a first direction forming a first angle with the radial direction, and at least a portion of the proximal expanded section extends in a second direction forming a second angle with the radial direction, wherein the first angle is less than the second angle.

3. The annuloplasty device according to claim 2, wherein the first direction is substantially parallel with the radial direction.

4. The annuloplasty device according to claim 1, wherein, when the proximal expandable portion is expanded, the bows extend with a curvature forming an apex positioned at a maximum expanded diameter (D) of the proximal expandable portion that is at least three times the diameter of the coronary sinus.

5. The annuloplasty device according to claim 4, wherein a ratio of the maximum expanded diameter (D) of the proximal expandable portion to the diameter of the coronary sinus is in the range of from 3:1 to 5:1.

6. The annuloplasty device according to claim 1, wherein the second sheath comprises a lumen extending in the longitudinal direction with a distal opening arranged distally to the inflatable unit and a proximal opening arranged between the inflatable unit and the proximal expandable portion, to allow blood flow between the distal opening and the proximal opening.

7. The annuloplasty device according to claim 6, further comprising a guide wire arranged to extend inside the lumen and to exit the lumen at the distal opening.

8. A medical system for treating a defective mitral valve having an annulus, said system comprising: the annuloplasty device of claim 1 and an annuloplasty implant for permanent fixation at the mitral valve annulus, wherein said annuloplasty implant comprises a helix-shaped loop structure, configured to be positioned on either side of said valve to retain a modified shape of the annulus caused by the movement of the distal anchoring portion anchored in the coronary sinus toward the reversibly expandable portion arranged against the tissue wall outside the entrance to the coronary sinus.

9. A method for treating a defective mitral valve having an annulus, said method comprising:

temporarily inserting a flexible, elongate displacement unit in a delivery state into a coronary sinus adjacent to the mitral valve, positioning a proximal expandable portion of said displacement unit against a tissue wall at the entrance of the coronary sinus, anchoring a distal anchoring portion of said displacement unit comprising an inflatable unit inside the coronary sinus by expanding the inflatable unit, activating the displacement unit to an activated state by moving the distal anchoring portion in a longitudinal direction of the displacement unit to reduce a distance between the distal anchoring portion and the proximal expandable portion such that the shape of the annulus is modified to a modified shape, fixating an annuloplasty implant at the mitral valve annulus having the modified shape, wherein said annuloplasty implant comprises a helix-shaped loop structure positioned on either side of the valve to retain the modified shape of the annulus and at least a portion of said helix-shaped loop structure conforms to a curvature of said annulus, and removing the elongate displacement unit after said fixating said annuloplasty implant wherein said positioning a proximal expandable portion comprises:

expanding bows extending in the longitudinal direction for apposition against the tissue wall and exerting a force against the tissue wall in the longitudinal direction towards the distal anchoring portion, whereby the bows are expanded in a radial direction, perpendicular to the longitudinal direction, by pushing a proximal portion of a sheath towards the distal anchoring portion and wherein the bows comprise elongated ribs formed in the sheath by elongated cuts in the sheath, extending in the longitudinal direction, whereby the bows are formed from the same material as the sheath.

10. The method according to claim 9, wherein anchoring the distal anchoring portion comprises inflating the inflatable unit in the great cardiac vein and/or, in the anterior interventricular branch or vein, and/or in the posterior vein and/or in the posterior ventricular vein of the heart.

11. The method according to claim 9, further comprising guiding the elongate displacement unit along a guide wire arranged to extend inside a lumen of the elongate displacement unit and to exit the lumen at an opening distally of the inflatable unit, wherein the lumen has a proximal opening arranged between the inflatable unit and the proximal expandable portion.

\* \* \* \* \*